(12) United States Patent
Heikkilä et al.

(10) Patent No.: US 6,911,565 B2
(45) Date of Patent: Jun. 28, 2005

(54) PROCESS FOR THE PRODUCTION OF XYLITOL

(75) Inventors: Heikki Heikkilä, Espoo (FI); Heikki Ojamo, Kirkkonummi (FI); Andrei Miasnikov, Kantvik (FI); Vili Ravanko, Clinton, IA (US); Matti Tylli, Kantvik (FI)

(73) Assignee: Danico Sweetners Oy, Espoo (FI)

( * ) Notice: Subject to any disclaimer, the term of this patent is extended or adjusted under 35 U.S.C. 154(b) by 0 days.

(21) Appl. No.: 10/255,362

(22) Filed: Sep. 26, 2002

(65) Prior Publication Data

US 2003/0125588 A1 Jul. 3, 2003

(30) Foreign Application Priority Data

Sep. 26, 2001 (FI) .............................. 20011889

(51) Int. Cl.$^7$ ......................... C07C 31/18; C07C 31/20; C07C 31/22; C07C 31/24; C07C 31/26
(52) U.S. Cl. ..................... 568/852; 568/861; 568/864; 435/94; 435/158; 435/190; 536/124; 536/127; 536/128
(58) Field of Search .............................. 568/852, 861, 568/864; 435/94, 158, 190; 536/124, 127, 128

(56) References Cited

U.S. PATENT DOCUMENTS

| | | |
|---|---|---|
| 3,607,648 A | 9/1971 | Kobe et al. |
| 3,784,408 A | 1/1974 | Jaffe et al. |
| 4,008,285 A | 2/1977 | Melaja et al. |
| 4,066,711 A | 1/1978 | Melaja et al. |
| 4,075,406 A | 2/1978 | Melaja et al. |
| 4,631,129 A | 12/1986 | Heikkila |
| 5,081,026 A | 1/1992 | Heikkila et al. |
| 5,096,820 A | 3/1992 | Leleu et al. |
| 5,238,826 A | 8/1993 | Leleu et al. |
| 5,411,880 A | 5/1995 | Izumori et al. |
| 5,631,150 A | 5/1997 | Harkki et al. |
| 5,637,225 A | 6/1997 | Heikkila |
| 5,714,602 A | 2/1998 | Beck et al. |
| 5,872,247 A | 2/1999 | Fleche et al. |

FOREIGN PATENT DOCUMENTS

| | | |
|---|---|---|
| EP | 0 716 067 A1 | 6/1996 |
| EP | 0807682 | 11/1997 |
| EP | 0 745 758 A1 | 2/1998 |
| FR | 1 518 510 | 3/1968 |
| FR | 2 641 545 | 7/1990 |
| FR | 2 772 788 | 6/1999 |
| WO | WO 91/15588 | 10/1991 |
| WO | WO 93/01299 | 1/1993 |
| WO | WO 93/19030 | 9/1993 |
| WO | WO 88/05467 | 7/1998 |
| WO | WO 01/53306 A2 | 7/2001 |

OTHER PUBLICATIONS

Gong, Cheng–Shung, et al. "Quantative Production of Xylitol from D–xylose by a High–Xylitol Producing Yeast Mutant", *Biotechnology Letters*, 3(3): 130–135 (1981).

Kuhad, Ramesh C., et al. "Optimization of xylanase production by a hyperxylanolytic mutant strain of *Fusarium oxysporum*", *Process Biochemistry*, 33(6): 641–647 (1998).

Itoh, Hiromichi, et al., "Purification and Characterization of D–Tagatose 3–Epimerase from *Pseudomanas* sp. ST–24", *Biosci. Biotech. Biochem.*, 58(12): 2168–2171 (1994).

Bruijn, J.M., et al., "Reactions of Monosaccharides in Aqueous Alkaline Solutions", *Sugar Technology Reviews*, 13: 21–52 (1986).

Bhuiyan, Shakhawat, et al. "A New Method for the Production of L–Lykose from Ribitol Using Microbial and Enzymatic Reactions", *Journal of Fermentation and Bioengineering*, 86(5): 513–516 (1998).

Matsui, Masanao, et al., "Studies on 2–Keto–D–gluconic Acid", *Agr. Biol. Chem.*, 27(3): 180–184 (1963).

Abstract of Japanese Laid–Open Application No. 11113567, published Apr. 27, 1999.

Abstract of Japanese Laid–Open Application No. 8056659, published Mar. 5, 1996.

*Primary Examiner*—Elvis O. Price
(74) *Attorney, Agent, or Firm*—Scully, Scott, Murphy & Presser

(57) ABSTRACT

The present invention relates to a process for the production of xylitol. The process utilises ribulose for the preparation of xylitol and involves several different conversion reactions, such as reduction, epimerisation and/or isomerisation. The present invention also relates to the use of ribulose for the preparation of xylitol.

21 Claims, No Drawings

PROCESS FOR THE PRODUCTION OF XYLITOL

FIELD OF THE INVENTION

The present invention relates to a process for the production of xylitol. In particular, the invention relates to a process for the production of xylitol comprising conversion of ribulose.

BACKGROUND OF THE INVENTION

Xylitol is a naturally occurring 5-carbon sugar alcohol, which is present in small amount in many fruits and vegetables and is produced in the human body during normal metabolism. It has approximately the same sweetness as sucrose, lower caloric content of about 2.4 kcal/g, and it has certain known metabolic, dental and technical characteristics which make it an attractive special sweetener or sugar substitute in various contexts. For instance, xylitol is cariostatic and even anti-cariogenic. It is metabolised independently of insulin and can be safely consumed by non-insulin dependent diabetics, and it is non-toxic. Nowadays it is widely used in chewing gums, dental care products, health promoting products, functional food products, pharmaceutical products, confectionery products and the like.

Xylitol is usually prepared by processes utilizing natural raw materials, especially xylan-containing materials. In current use are methods in which a xylan-containing material is first hydrolysed to produce a mixture of monosaccharides, including D-xylose. After purification the D-xylose is then converted to xylitol, generally in a chemical process using e.g. a nickel catalyst such as Raney-nickel. A number of processes of this type have been described in the literature of the art. U.S. Pat. No. 3,784,408 (Jaffe et al.), U.S. Pat. No. 4,066,711 (Melaja et al.), U.S. Pat. No. 4,075,406 (Melaja et al.), U.S. Pat. No. 4,008,285 (Melaja et al.) and U.S. Pat. No. 3,586,537 (Steiner et al.) may be mentioned as examples.

The recovery of D-xylose during wood and pulp processing can be performed by various separation techniques. Chromatography is widely used. A process for the fractionation of sulfite spent liquor by chromatography is described in U.S. Pat. No. 5,737,225, Xyrofin Oy. The process uses a simulated moving bed including at least two chromatographic beds and, preferably, at least three different fractions are recovered, one of these being enriched with xylose and another with lignosulphonates. For instance U.S. Pat. Nos. 4,631,129; 4,008,285 and 4,075,406 also describe chromatographic processes for the recovery of xylose.

Processes in which microorganisms are utilised for biotechnological production of xylitol have also been described. It is known that many yeast strains produce reductase enzymes that catalyse the reduction of sugars to corresponding sugar alcohols. Many yeasts, in particular *Pichia, Candida, Hansenula* and *Kluyveromyces*, are also capable of reducing xylose to xylitol as an initial step in their xylose metabolism.

The reaction route or pathway of xylose utilisation for yeasts is in general the following: xylitol is synthesised in the first step by reduction of xylose to xylitol with the aid of xylose reductase. Xylitol is then metabolised by a series of successive steps. Xylitol is first oxidised to xylulose with xylitol dehydrogenase, xylulose is phosphorylated to xylulose-5-phosphate with xylulose kinase (also called xylulokinase), and then part of the xylulose-5-phosphate is converted to pyruvate via several intermediate steps. Also ethanol and $CO_2$ can be formed. The reactions are not tightly coupled, and the relevant main products and by-products vary depending on the yeast strain and the fermentation conditions, such as oxygen availability.

For instance PCT publications WO 90/8193, WO 91/0740, WO 88/5467 and French published application 2 641 545 describe the use of *Candida tropicalis, Candida guilliermondii* and *Candida parapsilosis*, respectively, for the industrial production of xylitol.

U.S. Pat. No. 5,081,026, Heikkilä et al., describes a process for the production of xylitol from xylose, in which an aqueous xylose solution is fermented with a yeast strain capable of converting free xylose to xylitol and free hexoses to ethanol. After fermentation, a xylitol-rich fraction is obtained by chromatographic separation, and finally, xylitol is recovered from said fraction.

Genetic modification of microorganisms in order to enhance their xylitol production have also been reported in the literature of the art. For example, in WO 91/15588, Hallborn, J. et al. describe the cloning of the xylose reductase gene from *Pichia stipitis* into *Saccharomyces cerevisiae*. Gong C. et al., *Biotechnol. Letters* 3:125–130 (1981) describe two high xylitol producing yeast mutants denominated HXP1 and HXP2, obtained after UV-mutagenesis of a wild strain of *Candida tropicalis* which originally was capable of metabolising D-xylose into xylitol.

EP 0 604 429, Xyrofin, describes novel yeast strains with modified xylitol metabolism, a process for the production of said strains, and the use of said strains in a process for producing xylitol. The strains are capable of reducing xylose into xylitol, but are deficient in one or more enzymes involved in the xylitol metabolism, with the effect that the xylitol produced accumulates in the culture medium and can be recovered therefrom. The yeasts described belong to the genera *Candida, Hansenula, Kluyveromyces* or *Pichia*, and the genetic modification eliminates or reduces expression of the gene that encodes xylitol dehydrogenase or xylulose kinase, or both.

Another approach that has been suggested for the bioproduction of xylitol is the enhancement of xylose production, thus providing more xylose as the primary metabolite for xylitol production.

Some fungi, including *Aureobasidium, Aspergillus, Trichoderma, Fusarium* and *Penicillium,* have been reported to have xylanolytic activity and thus be able to degrade xylan-containing biopolymers into xylose. E.g. Kuhad R. C. et al., *Process Biochemistry* 33:641–647 (1998) describe a hyperxylanolytic mutant strain of *Fusarium oxysporum* produced by UV and N-methyl-N'-nitro-N-nitrosoguanidine (NTG) treatment.

EP 0 672 161, Xyrofin, describes a method for the production of xylitol from carbon sources other than xylose and xylulose by using recombinant hosts. The microorganisms produce xylitol via an altered arabitol route involving in particular arabitol dehydrogenase, and/or via altered (over)expression of genes encoding the enzymes of the oxidative branch of the pentose phosphate pathway (PPP), in particular glucose-6-phosphate dehydrogenase or 6-phospho-D-gluconate dehydrogenase, thus enabling utilisation of glucose, for instance. When used, D-glucose is phosphorylated into D-glucose-6-phosphate and converted to D-ribulose-5-phosphate via 6-phospho-D-gluconate. The D-ribulose-5-phosphate is then epimerised to D-xylulose-5-phosphate, dephosphorylated to D-xylulose and reduced to xylitol. Amplification of glucose-6-phosphate dehydrogenase enzyme activity in osmotolerant yeasts is later also described in FR 2 772 788, Roquette Freres.

U.S. Pat. No. 5,096,820, Leleu et al., also describes a process in which xylitol is produced from D-glucose. Glucose is first microbiologically converted to D-arabitol, which likewise is microbiologically converted to D-xylulose. The D-xylulose is then enzymatically isomerised into a mixture of D-xylose and D-xylulose, which is catalytically hydrogenated. Finally, the xylitol is recovered by chromatographic separation or crystallisation. The D-arabitol containing fractions, or the mother liquor from crystallization, which are rich in xylitol but also in D-arabitol, are preferably recirculated into the process. U.S. Pat. No. 5,238,826, Leleu et al., uses a similar process to obtain D-xylose, ultimately for the preparation of xylitol by hydrogenation. Also in this process, D-glucose is first microbiologically converted to D-arabitol, which then likewise is microbiologically converted to D-xylulose. The D-xylulose is then enzymatically isomerised into a mixture of D-xylose and D-xylulose. Finally, the mixture is subjected to chromatographic separation, the D-xylose fraction is recovered and the D-xylulose fraction is recirculated into the isomerisation step.

The background art thus describes the production of xylitol from naturally occurring raw materials. At present, the raw materials mainly used are xylan-containing materials. From xylan, xylitol is produced by chemical processes or combinations of chemical and biological processes. Further, processes utilising microorganisms, in particular yeasts, capable of producing xylitol from monosaccharide solutions or pure D-xylose solutions have been described.

In view of the increasing use of xylitol, in particular due to its properties as sweetener and therapeutic effects, new methods for the production of xylitol would be welcome. In particular, there is an expressed need for processes for the production of xylitol from other sources than those mainly utilised.

U.S. Pat. No. 5,714,602, Cerestar Holding B.V., discloses a process developed from the this viewpoint. According to the document, xylitol is produced from gluconic acid. In a first step, gluconic acid is decarboxylated, by using sodiumhypochlorite or hydrogen peroxide into arabinose, which through hydrogenation is converted into arabinitol. After epimerisation, a mixture of xylitol, ribitol and D,L-arabinitol is obtained, from which xylitol is recovered by chromatographic methods.

EP 754 758, Cerestar Holding B.V., relates to a process for the production of xylitol in two steps. In the first step a hexose is converted to a pentitol by fermentation, and in the second step the pentitol is catalytically isomerised to yield a pentitol mixture. Specifically, the document describes a process in which glucose is fermented to arabinitol and then isomerised into a pentitol mixture containing xylitol, ribitol and D,L-arabinitol. Xylitol can be recovered from said mixture by chromatographic methods.

WO 93/1903, Amylum, also describes a process for the production of xylitol from monosaccharides, in particular D-glucose, D-fructose, D-galactose, L-sorbose or mixtures thereof. The starting material is first oxidized to D-arabinonic acid, D-lyxonic acid, and/or L-xylonic acid and the intermediate is then hydrogenated in one or several steps to a product consisting mainly of xylitol or a mixture of xylitol, arabinitol and ribitol. Finally, if necessary, xylitol is separated by means of chromatography.

SHORT DESCRIPTION OF THE INVENTION

The present invention is based on the utilisation of ribulose for xylitol production. Surprisingly, it has been found that xylose can be produced from ribulose by a simple process comprising at least one of the following two conversion reactions, epimerisation and isomerisation. Eventually, xylose is converted to xylitol.

It is thus an object of the present invention to provide a process for the preparation of xylitol from ribulose by reduction and at least one of epimerisation and isomerisation.

In a preferred embodiment of the invention, the process for the preparation of xylitol utilises a mixture of ribulose and xylulose as starting material.

In another preferred embodiment, the process also involves at least one separation step. In particular, chromatographic separation is used.

In still a preferred embodiment of the present invention, some of the fractions, in particular xylulose- and ribulose-containing fractions, obtained in the separation step(s) are recirculated into the isomerisation and/or epimerisation steps.

In accordance with the present invention, the processes can be carried out chemically, microbiologically, or enzymatically.

Further, the reactions can be carried out simultaneously, in parallel or sequentially.

The present invention also describes processes for the preparation of ribulose. Also processes for the preparation of mixtures of ribulose and xylulose are described.

Furthermore, processes for the purification and recovery of the products are described. Preferably, xylose and xylitol are recovered by crystallization.

Still further, the invention relates to the use of ribulose for the preparation of xylitol.

DETAILED DESCRIPTION OF THE INVENTION

The present invention is thus based on utilisation of ribulose. Previously, ribulose has been regarded as disadvantageous in xylitol production. Fermentation is widely used as a first step in the process, and fermentation always yields a mixture which is problematic when considering the further processing. This is particularly the case when using glucose as the starting material for fermentation. In accordance with the present invention, instead of being a harmful by-product in the process, ribulose can be utilised as an advantageous starting material for xylitol production. In particular, xylitol can be produced from both xylulose and ribulose, without experiencing problems in the xylulose-xylose route.

The process according to the invention utilises at least two steps, reduction, epimerisation and/or isomerisation for conversion of ribulose. In the process, both D- and L-ribulose can be used.

In connection with the present invention, isomerisation is defined as an equilibrium reaction between aldoses and ketoses, and epimerisation is defined as an equilibrium reaction between ketoses.

The epimerisation reaction can preferably be carried out by using an enzyme having ketose 3-epimerase (tagatose epimerase) activity, and thus being able to convert ribulose to xylulose. A suitable enzyme for carrying out the epimerisation process has been described for instance in U.S. Pat. No. 5,411,880, Izumori et al., disclosing the enzyme D-ketohexose 3-epimerase obtained from *Pseudomonas cichorii* ST-24, FERM BP-2736. The enzyme epimerises D-ketohexoses, D-ketopentoses and L-ketopentoses at their C-3 positions to form their corresponding epimeric counterparts. The examples show e.g. the interconversion reactions of D-xylulose and D-ribulose, and L-xylulose and L-ribulose, respectively. In Biosci. Biotech. Biochem. 58 (1994) 2168–2171, where the inventors are coauthors, the same enzyme is described but renamed as D-tagatose 3-epimerase. It is pointed out that the enzyme epimerises free keto-sugars but not phosphorylated sugars, and is more active on ketoses with cis than trans configuration.

The reaction can be carried out by using both isolated and purified enzyme preparations as well as microorganisms expressing such enzyme activity. The gene for tagatose epimerase is known and has been successfully cloned and expressed e.g. in E. coli (Ishida, Y., Kamiya, T., Itoh, H., Kimura, Y., Izumori, K. J. Ferment. Bioeng. 83 (1997) 529–534). Suitable production systems can hence also be constructed by genetic engineering.

The ketose 3-epimerase enzyme is able to epimerise several hexuloses and pentuloses at their 3-carbon. Due to the reversibility of the reaction, a mixture is usually formed. Starting with D-ribulose, a mixture of D-ribulose and D-xylulose is formed, which in equilibrium contains about 85% D-xylulose. The same equilibrium is also formed when starting from a mixture of D-ribulose and D-xylulose.

The isomerisation reaction can be carried out chemically, microbiologically, or enzymatically. For enzymatic isomerisation, an enzyme having glucose isomerase or xylose isomerase acticity can be used. The enzyme catalyses the conversion of xylulose to xylose. Such enzymes are commercially available. As one example, Spezyme GI, Genencor Int., Finland, may be mentioned. It has been analysed that Spezyme Gl effects some amounts of conversation between ribulose and ribose. Preferably, an enzyme that does not isomerise D-ribulose is used. Also this reaction can naturally be carried out by using both isolated and purified enzyme preparations and natural or genetically engineered microorganisms expressing such enzyme activity. Chemically, the reaction can be carried out for instance by alkaline isomerisation, as described e.g. by de Bruijn et al., SugarTechnology Reviews 13 (1986) 21–52.

For enzymatic conversions, immobilized or free enzymes can be used, for instance in continuously stirred tank reactions (CSTR). Preferably, the conversions are carried out with immobilised enzymes in continuous flow columns. The reactions are reversible and the compounds and yields obtained will depend on the equilibrium constants and the conditions used. Usually, compound mixtures are obtained. Both enzymatic steps, however, favour the formation of the preferable products. The epimerisation and isomerisation reactions can be performed sequentially in either order, in parallel or simultaneously.

The reduction reaction can also be performed chemically, enzymatically or microbiologically. Chemical reduction, by using e.g. hydrogenation, metal borohydride, amalgam, or electrochemical reduction is regarded as preferred. Most preferably, catalytic hydrogenation is used.

Preferably, the process according to the invention also comprises at least one separation step. Preferably, chromatographic separation is used. The chromatographic separation can be performed at different stages of the process, and the process can involve several different separation steps. When, for instance, the process according to the invention is carried out by using ribulose/xylulose as a starting material, and performing isomerisation as the first step, a mixture of ribulose, xylulose and xylose is obtained. From this mixture, xylose can be separated, whereafter an epimerisation reaction may be carried out on the remaining mixture of ribulose and xylulose. In addition to chromatographic separation, fractions can be separated or purified by using crystallization, ion exchange, membrane processes, such as ultrafiltration, nanofiltration, or electrodialysis, for instance.

Alternatively, the order can be reversed, but the separation step conserved. In such a case, epimerisation of ribulose/xylulose will give a mixture enriched with xylulose. After separation of ribulose, isomerisation is carried out on the xylulose fraction.

A still further alternative is to carry out epimerisation and isomerisation first, and optionally carry out separation as a final step.

The reactions can thus be carried out sequentially in the desired order. It is also possible to perform the reactions simultaneously, for example in a CSTR or continuous flow column containing the enzymes or microbes needed.

The process according to the present invention can also involve other reactions, for example catalytical alditol epimerisation.

A preferred alternative is to recirculate products obtained in the reactions back into the process.

For instance, ribulose, or a mixture of ribulose and xylulose, can be epimerised, whereby a mixture enriched with xylulose, but also containing ribulose, is obtained. As shown in the examples, the mixture can contain different amounts of ribulose and xylulose, for instance about 15% of ribulose and about 85% of xylulose. Isomerisation of said mixture will yield a mixture of xylose, xylulose and ribulose. Starting from the relative proportions mentioned above, e.g. a mixture of 70% xylose, 15% of xylulose and 15% of ribulose can be obtained. Said components can be separated, for instance by chromatographic separation, yielding a fraction enriched with xylose, a fraction containing ribulose and a fraction containing xylulose. The xylose fraction can be purified and xylose recovered therefrom e.g. by crystallization. The xylose can also, directly or in purified form, be hydrogenated into xylitol. The ribulose fraction is preferably recirculated back to the epimerisation reaction, and the xylulose fraction is preferably recirculated back to the isomerisation reaction.

Each of the mixtures can be hydrogenated, the hydrogenation resulting in a mixture of ribitol, arabitol (=arabinitol) and xylitol, from which xylitol can be separated and recovered. Fractions containing ribitol, arabitol and/or xylitol, obtained in said separation, can be recirculated back to the hydrogenation step. The starting material, ribulose, can also be isomerised to ribose, and then hydrogenated and epimerised to ribitol, xylitol, DL-arabitol containing pentitol mixture as already described.

A further alternative is to subject the ribulose/xylulose mixture obtained after epimerisation, or fermentation, to a separation process. The ribulose containing fraction obtained in said separation is then circulated back into the epimerisation process, and the xylulose containing fraction obtained is circulated back into the isomerisation process for production of xylose, or used for hydrogenation. Hydrogenation of xylulose results in a mixture of arabitol and xylitol. These components can be separated from each other e.g. by chromatographic separation as described in the examples and as known from the literature for example (U.S. Pat. No. 4,008,285).

The epimerisation and isomerisation of ribulose yield xylose as the main product. Other products, such as xylulose, ribitol, and arabitol, obtained during the process can also be recovered. However, these products can also be recirculated into the process in order to improve the xylose/xylitol yield. The xylose obtained is eventually converted to xylitol by enzymatic or microbiological reduction. Chemical reduction, by using e.g. hydrogenation, metal boro hydride, amalgam, or electrochemical reduction, is regarded as preferred. Most preferably, catalytic hydrogenation is used. Before the chemical reduction reactions the solutions can be purified e.g. by using ion exchange methods in order to improve the reaction performance, i.a. for extending the life time of the catalyst.

The starting material for the process is ribulose. A mixture of ribulose and xylulose can also be used.

Some microorganisms are able to produce ribulose. Ribulose is thus a naturally occurring compound. However, processes for preparing ribulose in industrial scale have been scarcely reported, and ribulose is not commercially available.

Ribulose, and xylulose, can be prepared from D-glucose for instance by microbiological fermentation. D-glucose is an abundant natural compound and commercially available at low cost. D-glucose is thus a preferred raw material for ribulose preparation.

In connection with the present invention, some *Bacillus* strains have been shown to convert glucose with 30–50 wt % yields to a mixture of D-ribulose and D-xylulose. Such strains can be obtained by screening natural mutants, by conventional mutagenesis, and by genetic engineering. Strains that have been genetically engineered for the purposes of the present invention have been shown to produce ribulose/xylulose 2:1 mixtures in a yield of about 35 wt % in non-optimised conditions.

Ribulose, and xylulose, can also be obtained for instance by isomerisation of ribose. Isomerisation can be performed both chemically, microbiologically, and enzymatically. A suitable method for isomerisation of L-ribose has been described e.g. in U.S. Pat. No. 6,037,153, Hayashibara Biochem Lab. Production of D-ribose has been described in U.S. Pat. No. 3,607,648, Takeda Chem. Ind. Ltd.

Other sources for ribulose and xylulose production are for instance 2-keto-L-gulonic acid and 2-keto-D-gluconic acid.

In connection with the present invention, the starting material is preferably produced by fermentation.

Examples of suitable agents and methods for carrying out the appropriate reactions are disclosed in the literature of the art. For instance, production of D-ribulose and D-xylulose by fermentation with *Brevibacterium* sp., ATCC 21049, and *Corynebacterium* sp., ATCC 21050, is described in FR 1,518,510, Kyowa Ferm. Ind. Co., Ltd and CA 840,981, Kyowa Hakko Kogyo Co. The strains are commercially available. As examples of suitable carbon sources, saccharides, such as glucose, fructose, maltose, sucrose, starch, starch hydrolysate, molasses, and glycerol, mannitol, sorbitol, and organic acids are mentioned.

A ribitol dehydrogenase capable of forming D-ribulose from ribitol in the presence of NAD+ has been described in JP 8056659, Hayashibara Seibutsu Kagaku. A thermostable D-arabinitol dehydrogenase capable of oxidizing D-arabinitol to D-ribulose has been described in JP 11113567, Ikeda Shokuken KK and Nippon Kayaku Ltd. The enzyme is, however, suggested for use as a diagnostic for candidiasis. A dehydrogenase gene from *Pichia stipitis* having D-arabinitol dehydrogenase activity and capable of producing D-ribulose from D-arabinitol has been described by Hallborn et al., Yeast (England) July 1995, 11 (9) pp. 839–847.

JP 11018792, Mitsubishi Chem Corp, describes micrororganisms capable of converting ribitol to L-ribulose. The microorganisms mentioned belong to the genus *Gluconobacter, Acetobacter, Alcaligenes* and *Acinetobacter; Gluconobacter frateurii* IFO 02508 is mentioned as preferred. Mutants of *Klebsiella aerogenes* W70 which are constitutive for L-fucose isomerase have been shown to produce D-ribulose from D-arabinose by Charnetsky et al. J. Bacterol. 119 (1974)162–169. A thiamine-requiring *Corynebacterium* strain producing D-ribulose from gluconic acid has been described in JP 45039034, Godo Shusei Co., Ltd.

Stereospecific oxidation of polyols and sugars to form corresponding ketoses and carbonyl sugars, respectively, has been described by Huwig et al., Meded. Fac. Landbouwwet. Rijksuniv. Gent. 59 (1994)2393–2401. The bioconversion reactions were performed by using *Pseudomonas* sp. L-glucitol dehydrogenase (GDH) and *Peniophora gigantea* immobilised pyranose oxidase (PO, EC 1.1.3.10). By using L-arabitol as the substrate, 60% conversion to L-xylulose/L-ribulose (4:1) was obtained.

Shakhawat et al., Journal of Fermentation and Bioengineering 86 (1998) 5, pp. 513–516, describe the preparation of L-lyxose from ribitol by a microbial oxidation reaction, which yields L-xylulose as an intermediate.

PCT EP99/09771, Xyrofin Ltd., describes a process for the production of L-ribose from L-arabinose. The L-ribose can be used for the preparation of L-ribulose e.g. by isomerisation.

Decarboxylation of 2-ketoaldonic acids has been described by Matsui, M, Uchiyama, M. and Liau, Agr. Biol. Chem. 27(1963) 3, p. 180–184. The authors present a scheme for the decarboxylation of 2- and 3-ketoacids into corresponding ketoses and aldoses, and elaborate on the importance of a metal ion catalyst. Nickel ion catalysed decarboxylation of 2-keto-D-gluconic acid in pyridine yielded D-ribulose as the main product. In addition, D-arabinose was found in a smaller amount. Decarboxylation of 2-keto-L-gulonic acid, on the other hand, yielded L-xylose and L-xylulose in approximately equal amounts. It is mentioned that D-arabinose and L-xylose possibly are formed from the main products D-ribulose and L-xylulose due to an alkaline isomerisation process mediated by the pyridine used. An improved method avoiding both the use of pyridine which is harmful in itself, and the isomerisation process, is described in U.S. Pat. No. 5,872,247, Duflot, P. and Fleche, G. The nickel ion catalysed decarboxylation process is performed by putting an aqueous solution of 2-ketoaldonic acid in contact with a resin carrying vinylpyridine groups. According to the document, the process allows for obtaining the ketose of the corresponding functionality immediately lower than the ketoaldonic acid in high yield and purity. D-ribulose is disclosed as the decarboxylation product of 2-keto-D-gluconic acid, D-xylulose of 2-keto-D-galactonic acid, and D-erythrulose of 2-keto-D-arabinonic acid, respectively.

The ribulose prepared can be separated and purified. It can be used, for instance, for the preparation of ribitol.

In connection with the present invention, the ribulose obtained is preferably utilised for the production of xylose and xylitol as outlined above.

The invention will be described in detail in the following specific examples. The examples are included herein for illustrative purposes only and are not to be construed as limiting or restricting the scope of the invention in any way.

EXAMPLE 1

Production of a D-xylulose/D-ribulose Mixture

The mutant *Bacillus subtilis* strain GX7 described in PCT patent application PCT/FI01/00051 was cultivated on a LB (Luria broth) medium containing 50 g/l glucose under aerobic conditions at 30° C. in a shake flask. After 120 hours the glucose was converted to 9.8 g/l D-ribulose and 3.3 g/l D-xylulose. The cellmass was then separated from the fermentation broth by centrifugation and the clarified broth was concentrated under vacuum to 1/10 of the original volume.

EXAMPLE 2
Production of a D-xylulose/D-ribulose Mixture

*Corynebacterium* sp. ATCC 21050 was cultivated in a shake flask under aerobic conditions at 30° C. in a medium containing in tap water 100 g/l glucose, 5 g/l yeast extract, 6 g/l urea, 30 ug/l biotin, 10 g/l MgSO$_4$x7H$_2$O and 20 g/l KH$_2$PO$_4$. The pH was adjusted to 8 before inoculation with an overnight aerobic culture in a medium containing 20 g/l glucose, 10 g/l yeast extract, 10 g/l peptone and 2.5 g/l NaCl. After 120 hours the glucose was converted to 13.6 g/l D-ribulose and 12.2 g/l D-xylulose.

EXAMPLE 3
Enrichment of D-xylulose Through Epimerisation

Epimerisation was performed on the clarified concentrate obtained in example 1. The pH of the concentrate was adjusted to 7.5, 10 units/ml of tagatose epimerase was added and the reaction was carried out for 2 hours at 30° C. The tagatose epimerase was produced as described in Itoh et al. (1994). 71.2 g/l D-xylulose and 46.6 g/l D-ribulose was analyzed in the reaction mixture after the 2 hours.

EXAMPLE 4
Chromatographic Separation of Ribulose and Xylulose

An epimerisation reaction mixture containing ribulose and xylulose was purified by applying chromatographic separation. The ribulose content was about 14% on DS (dry substance) and the xylulose content about 81% on DS. The rest or about 5% on DS comprised salts and neutral compounds.

The separation was made in a laboratory scale column (diameter 0.1 m) as a batch process. A strongly acid cation exchange resin in Ca$^{2+}$ form was used, the bed height was about 1.5 m. The cross-linkage degree of the resin was 5.5% and the average particle size 0.3 mm. A feed having a concentration of 35 g/100 ml was used. The separation temperature was 65° C. and the flow rate 50 ml/min. The separation was performed as follows:

Step 1.

About 700 ml of feed solution was introduced to the top of the resin bed. The feed and the column were preheated to 65° C.

Step 2.

The feed solution was eluted downwards the column by feeding deionised water to the top of the resin bed. The eluent was also preheated to 65° C. The flow rate was controlled by an outflow pump.

Step 3.

The outflow of the column was monitored continuously by on-line dry substance (refractive index) device. The outflow was collected in separate fractions at 2 min interval.

Step 4.

The composition of the collected samples was analyzed with HPLC. According to this data, the outflow was pooled in two fractions and a capacity calculation of these two product fractions was made.

Table 1 presents the composition of the feed solution and the outflow fractions (purity and yield). Xylulose is eluting out faster than ribulose, but the higher amount of xylulose resulted in some overlapping of the profiles. In addition to this, the salts are mainly eluting into the xylulose fraction reducing the purity to some extent. Other neutral components are eluting in both product fractions.

The yield is calculated by dividing the amount of the target component in the target fraction by the amount of the target component in both outcoming fractions.

TABLE 1

Composition of feed solution and outflow fractions

| | Xylulose purity, % on DS | Ribulose purity, % on DS | Xylulose yield, % | Ribulose yield, % |
|---|---|---|---|---|
| Feed solution | 14 | 81 | — | — |
| Xylulose fraction | 96 | 2 | 90 | 10 |
| Ribulose fraction | 34 | 53 | 10 | 90 |

The xylulose fraction was isomerised to produce xylose, and the ribulose fraction was recirculated back to epimerisaton (for xylulose production).

EXAMPLE 5
Chromatographic Separation of Ribulose and Xylulose

An epimerisation reaction mixture containing ribulose and xylulose was purified by applying chromatographic separation. The ribulose content was about 15% on DS and the xylulose content about 85% on DS.

The separation was made in a laboratory scale column (diameter 0.1 m) as a batch process. A strongly acid cation exchange resin in Ca$^{2+}$ form was used, the bed height was about 1.5 m. The cross-linkage degree of the resin was 5.5% and average particle size 0.3 mm. A feed having a concentration of 35 g/100 ml was used. The separation temperature was 65° C. and the flow rate 50 ml/min. The separation was performed as follows:

Step 1.

About 700 ml of feed solution was introduced to the top of the resin bed. The feed and the column were preheated to 65° C.

Step 2.

The feed solution was eluted downwards in the column by feeding deionised water to the top of the resin bed. The eluent was also preheated to 65° C. The flow rate was controlled by an outflow pump.

Step 3.

The outflow of the column was monitored continuously by on-line dry substance (refractive index) device. The outflow was collected in separate fractions at 2 min interval.

Step 4.

The composition of the pooled samples was analyzed with HPLC and a capacity calculation of the two product fractions made.

Table 2 presents the composition of the feed solution and the outflow fractions (purity and yield) calculated as described in example 4. Elution behaviour was similar as in example 4.

TABLE 2

Composition of feed solution and outflow fractions

|  | Xylulose purity, % on DS | Ribulose purity, % on DS | Xylulose yield, % | Ribulose yield, % |
|---|---|---|---|---|
| Feed solution | 15 | 85 | — | — |
| Xylulose fraction | 98 | 2 | 90 | 10 |
| Ribulose fraction | 39 | 61 | 10 | 90 |

EXAMPLE 6
Chromatographic Separation of Ribulose and Xylulose

An epimerisation reaction mixture containing ribulose and xylulose was purified by applying chromatographic separation. The ribulose content was about 38% on DS and the xylulose content about 58% on DS. The rest or about 4% on DS comprised salts and other neutral compounds.

The separation was made in a laboratory scale column (diameter 0.1 m) as a batch process. A strongly acid cation exchange resin in $Ca^{2+}$ form was used, the bed height was about 1.5 m. The cross-linkage degree of the resin was 5.5% and the average particle size 0.3 mm. A feed having a concentration of 35 g/100 ml was used. The separation temperature was 65° C. and the flow rate 50 ml/min. The separation was performed as follows:

Step 1.

About 700 ml of feed solution was introduced to the top of the resin bed. The feed and the column were preheated to 65° C.

Step 2.

The feed solution was eluted downwards the column by feeding deionised water to the top of the resin bed. The eluent was also preheated to 65° C. The flow rate was controlled by an outflow pump.

Step 3.

The outflow of the column was monitored continuously by on-line dry substance (refractive index) device. The outflow was collected in separate fractions at 2 min interval.

Step 4.

The composition of the collected samples was analyzed with HPLC. According to this data, the outflow was collected in two pools and a capacity calculation of these two product fractions was made.

Table 3 presents the composition of the feed solution and the outflow fractions (purity and yield). Xylulose and ribulose were eluted similary as in example 4. Salts are mainly eluting into the xylulose fraction and other neutral components are eluting into both product fractions. Yields are calculated similarly as in example 4.

TABLE 3

Composition of feed solution and outflow fractions

|  | Xylulose purity, % on DS | Ribulose purity, % on DS | Xylulose yield, % | Ribulose yield, % |
|---|---|---|---|---|
| Feed solution | 38 | 58 | — | — |
| Xylulose fraction | 90 | 7 | 90 | 10 |
| Ribulose fraction | 14 | 81 | 10 | 90 |

EXAMPLE 7
Chromatographic Separation of Ribulose, Xylulose and Xylose

A reaction mixture containing ribulose, xylulose and xylose (produced according to the methods disclosed in example 10 or 11) was purified by applying chromatographic separation. The feed solution had a xylose purity of about 67% on DS and a ribulose and xylulose purity of about 14% on DS each. Some salts and neutral components (about 5% on DS in total) were also found.

The separation was made in a laboratory scale column (diameter 0.1 m) as a batch process. A strongly acid cation exchange resin in $Ca^{2+}$ form was used, the bed height was about 1.5 m. The cross-linkage degree of the resin was 5.5% and the average particle size 0.3 mm. A feed having a concentration of 35 g/100 ml was used. The separation temperature was 65° C. and the flow rate 50 ml/min. The separation was performed as follows:

Step 1.

About 700 ml of feed solution was introduced to the top of the resin bed. The feed and the column were preheated to 65° C.

Step 2.

The feed solution was eluted downwards the column by feeding deionised water to the top of the resin bed. The eluent was also heated to 65° C. The flow rate was controlled by an outflow pump.

Step 3.

The outflow of the column was monitored continuously by on-line dry substance (refractive index) and conductivity measurement device. The outflow was collected in separate fractions at 2 min interval.

Step 4.

The composition of the collected samples was analyzed with HPLC. According to this data, three fractions were pooled and a capacity calculation of these product fractions made.

Table 4 presents the composition of the feed solution and the three outflow fractions (purity and yield). Xylose is eluting out first, but the high amount of xylose in the feed resulted in an overlapping of xylose and xylulose. Salts are also eluting with the xylose fraction. Ribulose is eluting as a last component and only a small overlapping of xylulose and ribulose occurred. The other neutral components were left under xylulose and ribulose peaks.

The yield is calculated by dividing the amount of the target component in the target fraction by the amount of the target component in all outcoming fractions.

TABLE 4

Composition of feed solution and outflow fractions

|  | Xylose purity, % on DS | Xylulose purity, % on DS | Ribulose purity, % on DS | Xylose yield, % | Xylulose yield, % | Ribulose yield, % |
|---|---|---|---|---|---|---|
| Feed solution | 67 | 14 | 14 | — | — | — |
| Xylose fraction | 91 | 3 | 0 | 65 | 10 | 0 |
| Xylulose fraction | 63 | 32 | 2 | 35 | 85 | 5 |
| Ribulose fraction | 0 | 5 | 89 | 0 | 5 | 95 |

The xylulose fraction was used in an isomerisation reaction to produce xylose. The ribulose fraction was recirculated back to epimerisation (for xylulose production). From the xylose fraction, xylose was recovered by crystallization.

EXAMPLE 8
Chromatographic Separation of Ribulose, Xylulose and Xylose

A reaction mixture containing ribulose, xylulose and xylose was purified by applying chromatographic separation. The feed solution had a xylose purity of about 67% on DS, and a ribulose and xylulose purity of about 14% on DS, each. Some salts and neutral components (about 5% on DS in total) were also found.

The separation was made in a laboratory scale column (diameter 0.1 m) as a batch process. A strongly acid cation exchange resin in $Ca^{2+}$ form was used, the bed height was about 1.5 m. The cross-linkage degree of the resin was 5.5% and the average particle size 0.3 mm. A feed having a concentration of 35 g/100 ml was used. The separation temperature was 65° C. and the flow rate 50 ml/min. The separation was performed as follows:

Step 1.
About 700 ml of feed solution was introduced to the top of the resin bed. The feed and the column were preheated to 65° C.

Step 2.
The feed solution was eluted downwards the column by feeding deionised water to the top of the resin bed. The eluent was also preheated to 65° C. The flow rate was controlled by an outflow pump.

Step 3.
The outflow of the column was monitored continuously by on-line dry substance (refractive index) and conductivity measurement device. The outflow was collected in separate fractions at 2 min interval.

Step 4.
The composition of the collected samples was analyzed with HPLC. According to this data, two fractions were pooled and a capacity calculation of these product fractions made (xylose fraction and xylulose+ribulose rich fraction).

Table 5 presents the composition of the feed solution and the two outflow fractions (purity and yield). Again, xylose is eluting out first, but the high amount of xylose in the feed resulted in some overlapping of xylose and later eluting compounds. Salts are mainly eluting in the xylose fraction. Ribulose is eluting as a last component but it was collected in the same fraction with xylulose and some other neutral components.

The yields are calculated as in example 7.

TABLE 5

Composition of feed solution and outflow fractions

|  | Xylose purity, % on DS | Xylulose purity, % on DS | Ribulose purity, % on DS | Xylose yield, % | Xylulose yield, % | Ribulose yield, % |
|---|---|---|---|---|---|---|
| Feed solution | 67 | 14 | 14 | — | — | — |
| Xylose fraction | 91 | 3 | 0 | 65 | 10 | 0 |
| Xylulose + ribulose fraction | 45 | 24 | 27 | 35 | 90 | 100 |

The xylose fraction was used in a hydrogenation reaction to produce xylitol. The other product fraction was circulated back to epimerisation to produce more xylulose.

EXAMPLE 9
Chromatographic Separation of Ribulose, Xylulose and Xylose

A reaction mixture containing ribulose, xylulose and xylose was purified by applying chromatographic separation. The feed solution had a xylose purity of about 70% on DS, and a ribulose and xylulose purity of about 15% on DS each.

The separation was made in a laboratory scale column (diameter 0.1 m) as a batch process. A strongly acid cation exchange resin in $Ca^{2+}$ form was used, the bed height was about 1.5 m. The cross-linkage degree of the resin was 5.5% and average particle size 0.3 mm. A feed having a concentration of 35 g/100 ml was used. Separation temperature was 65° C. and flow rate 50 ml/min. The separation was performed as follows:

Step 1.
About 700 ml of feed solution was introduced to the top of the resin bed. The feed and the column were preheated to 65° C.

Step 2.

The feed solution was eluted downwards in the column by feeding deionised water to the top of the resin bed. The eluent was also preheated to 65° C. The flow rate was controlled by an outflow pump.

Step 3.

The outflow of the column was monitored continuously by on-line substance (refractive index) device. The outflow was collected in separate fractions at 2 min interval.

Step 4.

The composition of the collected samples was analyzed with HPLC and capacity calculation of the three product fractions made.

Table 6 presents the composition of the feed solution and the outflow flow fractions (purity and yield) calculated as in example 4. Xylose is eluting out first, but the high amount of xylose in feed resulted in an overlapping of xylose and xylulose. Ribulose is eluting as a last component and only a small overlapping of xylulose and ribulose occurred.

TABLE 6

Composition of feed solution and outflow fractions

| | Xylose purity, % on DS | Xylulose purity, % on DS | Ribulose purity, % on DS | Xylose yield, % | Xylulose yield, % | Ribulose yield, % |
|---|---|---|---|---|---|---|
| Feed solution | 70 | 15 | 15 | — | — | — |
| Xylose fraction | 97 | 3 | 0 | 65 | 10 | 0 |
| Xylulose fraction | 64 | 34 | 35 | 35 | 85 | 5 |
| Ribulose fraction | 0 | 5 | 95 | 0 | 5 | 95 |

The xylulose fraction was used in isomerisation to produce xylose and the ribulose fraction was sent back to epimerisation (for xylulose production). The xylose fraction was used in hydrogenation to produce xylitol.

EXAMPLE 10
Isomerisation of the D-xylulose to D-xylose

A D-xylulose fraction obtained through chromatographic separation was concentrated to a concentration of 400 g/l xylulose. The pH of the concentrate was adjusted to 7.0 and 30 U/ml glucose isomerase (Sweetzyme, Novo Nordisk AS) was added. The reaction was carried out at 45° C. for 4 hours. 311 g/l D-xylose and 73 g/l D-xylulose was analyzed in the mixture after the reaction.

EXAMPLE 11
Isomerisation of Xylulose Without Prior Separation

The solution after xylulose enrichment such as in example 3 can also be isomerised with xylose (glucose) isomerase without prior chromatographic separation of the sugars. To effect this, a solution containing 43.2 g/l D-ribulose and 72.1 g/l D-xylulose was isomerised for 2 hours at 60° C. after addition of 1.66 g/l of glucose isomerase (Sweetzyme, Novo). After the isomerisation 21.9 g/l D-xylulose, 48.3 g/l D-xylose, 40.8 g/l D-ribulose and 1.1 g/l D-ribose were analyzed by HPLC.

EXAMPLE 12
Production of a Mixture of Ribitol and Arabinitol by Hydrogenation of Ribulose Ribulose solution from the fractions described in example 4, 5 or 6 was purified by an ion exchange method as described in example 17 and reduced to ribitol and arabinitol by hydrogenating ribulose syrup at a temperature of 100° C. and a pressure of 45 bar in an agitated batch autoclave using Raney-nickel as catalyst. The catalyst load was 10% wet catalyst of total solids of the syrup. The pH of the feed syrup was adjusted to 6 before the reaction. The dry substance of the feed was 50%. Hydrogenation time was three hours. The conversion of ribulose was over 90% and it yielded a 50/50 percent mixture of ribitol and arabinitol.

EXAMPLE 13
Production of a Mixture of Xylitol and Arabinitol by Hydrogenation of Xylulose Xylulose solution from the fractions described in example 4, 5 or 6 was purified by an ion exchange method as described in example 17 and hydrogenated to xylitol and arabinitol by reducing xylulose syrup at a temperature of 100° C. at 45 bar pressure in an agitated batch autoclave. The catalyst load was 10% wet catalyst of total solids of the syrup. The catalyst was Raney-nickel. The pH of the feed syrup was adjusted to 6 before the reaction. The dry substance of the feed was 50%. Hydrogenation time was three hours. The conversion of xylulose was more than 90% and the product was a 50/50 percent mixture of xylitol and arabinitol

EXAMPLE 14
Production of a Mixture of Ribitol, Xylitol and Arabinitol by Hydrogenation of Ribulose Ribulose solution from the fractions described in example 4, 5 or 6 was purified by an ion exchange method as described in example 17 and reduced to ribitol, xylitol and arabinitol by hydrogenating ribulose syrup at a temperature of 120° C. and a pressure of 70 bar in an agitated batch autoclave using Raney-nickel (Chemcat J 10 GS) as catalyst. The catalyst load was 80% wet catalyst of total solids of the syrup. The pH of the feed syrup was adjusted to 6 before the reaction. The dry substance of the feed was 50%. Hydrogenation time was twenty hours. The conversion of ribulose yielded 55% ribitol, 10% xylitol, 30% arabinitol and 3% others.

EXAMPLE 15
Production of a Mixture of Xylitol, Ribitol and Arabinitol by Hydrogenation of Xylulose Xylulose solution from the fractions described in example 4, 5 or 6 was purified by an ion exchange method as described in example 17 and hydrogenated to xylitol, ribitol and arabinitol by reducing xylulose syrup at a temperature of 120° C. and a pressure of 70 bar in an agitated batch autoclave. The catalyst load was 80% wet catalyst of total solids of the syrup. The catalyst was Raney-nickel. The pH of the feed syrup was adjusted to 6 before the reaction. The dry substance of the feed was 50%. Hydrogenation time was 24 hours. The conversion of xylulose yielded 60% xylitol, 30% arabinitol, 8% ribitol and 2% others.

EXAMPLE 16
Chromatographic Separation of Xylose and Xylulose

An isomerisation reaction mixture containing xylose and xylulose (obtained according to the method described in examples 4 and 10) was purified by applying chromatographic separation. The xylose content was about 78% on DS and the xylulose content about 17% on DS. The rest or about 5% on DS comprised salts and neutral compounds.

The separation was made in a laboratory scale column (diameter 0.1 m) as a batch process. A strongly acid cation exchange resin in $Ca^{2+}$ form was used, the bed height was about 1.5 m. The cross-linkage degree of the resin was 5.5% and the average particle size 0.3 mm. A feed having a concentration of 35 g/100 ml was used. The separation temperature was 65° C. and the flow rate 50 ml/min. The separation was performed as follows:

Step 1.
About 700 ml of feed solution was introduced to the top of the resin bed. The feed and the column were preheated to 65° C.

Step 2.
The feed solution was eluted downwards the column by feeding deionised water to the top of the resin bed. The eluent was also preheated to 65° C. The flow rate was controlled by an outflow pump.

Step 3.
The outflow of the column was monitored continuously by on-line dry substance (refractive index) device. The outflow was collected in separate fractions at 2 min interval.

Step 4.
The composition of the collected samples was analyzed with HPLC. According to this data, the outflow was pooled in two fractions and a capacity calculation of these two product fractions was made.

Table 7 presents the composition of the feed solution and the outflow fractions (purity and yield). Xylose is eluting out faster than xylulose, but the high amount of xylose resulted in some overlapping of the profiles. In addition to this, the salts are also eluting into the xylose fraction reducing the purity to some extent. Other neutral components are eluting in both product fractions.

Yields are calculated as in previous examples.

TABLE 7

Composition of feed solution and outflow fractions

|  | Xylose purity, % on DS | Xylulose purity, % on DS | Xylose yield, % | Xylulose yield, % |
|---|---|---|---|---|
| Feed solution | 78 | 17 | — | — |
| Xylose fraction | 93 | 3 | 75 | 10 |
| Xylulose fraction | 53 | 42 | 25 | 90 |

The xylulose fraction was recirculated back to isomerisation to produce more xylose, and the xylose fraction was used in a hydrogenation reaction to produce xylitol.

EXAMPLE 17
Purification of Xylose

The xylose product of a ribulose/xylulose/xylose-separation process according to example 9 was purified before the conversion step. The purification was made using a strongly acid cation exchange resin (Purolite C 150) and a weakly basic anion exchange resin (Dow 66). The temperature during the purification step was 40° C. and the flow rate 2–3 bed volumes in hour. The syrup concentration was 150 9/1.

EXAMPLE 18
Hydrogenation of Xylose to Xylitol

The purified xylose obtained in example 14 was subjected to a hydrogenation reaction. The hydrogenation was carried out in a stirred batch autoclave. The hydrogen pressure was 40 bar and the temperature 110° C. The mixing speed was 800 rpm. As catalyst, Raney nickel was used in a dosage of 10% wet catalyst per syrup dry substance. The hydrogenation time was three hours, the reducing sugar content after hydrogenation was <0.1% and the xylitol content 95.5%. The xylitol produced can be recovered e.g. as a crystalline product (as described by Jaffe in U.S. Pat. No. 4,066,711).

What is claimed is:

1. Process for the preparation of xylitol from ribulose comprising the steps of:
    epimerizing and isomerizing ribulose to form a mixture of ribulose, xylulose and xylose;
    chromatographically separating a xylose-rich fraction; and
    reducing said xylose-rich fraction into a xylitol-rich fraction.

2. Process for the preparation of xylitol from ribulose comprising the steps of:
    reducing and epimerizing ribulose to a mixture of ribitol, arabitol and xylitol; and
    chromatographically separating of a xylitol-rich fraction.

3. Process according to claim 2, comprising catalytic epimerisation of alditols.

4. Process according to claim 1 or 2, wherein a mixture of ribulose and xylulose is used as starting material.

5. Process according to claim 1 or 2, wherein part of the fractions obtained in said chromatographic separation step are recirculated into the isomerisation and/or epimerisation.

6. Process according to claim 5, wherein the fractions containing ribulose and xylulose are recirculated.

7. Process according to claim 1 or 2, wherein said epimerization and isomerization steps are carried out simultaneously or in series.

8. Process according to claim 7, wherein epimerisation is carried first, followed by isomerisation.

9. Process according to claim 7, wherein isomerisation is carried out first, followed by epimerisation.

10. Process according to claim 1 or 2, wherein ribulose is prepared by fermentation.

11. Process according to claim 1 or 2, wherein xylose is reduced to xylitol by hydrogenation.

12. Process according to claim 1 or 2, wherein xylitol is recovered.

13. Process according to claim 1 or 2, wherein xylitol is recovered by crystallization.

14. Process according to claim 3 wherein said epimerization and isomerization steps are carried out simultaneously or in series.

15. Process according to claim 4 wherein said epimerization and isomerization steps are carried out simultaneously or in series.

16. Process according to claim 10 wherein glucose is fermented to produce said ribulose.

17. Process according to claim 3 wherein xylose is reduced to xylitol by hydrogenation.

18. Process according to claim 4 wherein xylose is reduced to xylitol by hydrogenation.

19. Process according to claim 3 wherein xylitol is recovered by crystallization.

20. Process according to claim 4 wherein xylitol is recovered by crystallization.

21. Process according to claim 1 comprising recovering xylose from said xylose-rich fraction by crystallization; and converting said crystalline xylose to xylitol.

* * * * *

UNITED STATES PATENT AND TRADEMARK OFFICE
CERTIFICATE OF CORRECTION

PATENT NO. : 6,911,565 B2
DATED : June 28, 2005
INVENTOR(S) : Heikki Heikkila et al.

It is certified that error appears in the above-identified patent and that said Letters Patent is hereby corrected as shown below:

Title page,
Item [73], Assignee, "Danico Sweetners Oy, Espoo FI" should read -- Danisco Sweeteners OY, Espoo FI --.

Signed and Sealed this

Twenty-seventh Day of September, 2005

JON W. DUDAS
*Director of the United States Patent and Trademark Office*